United States Patent
Song et al.

(10) Patent No.: US 10,497,477 B2
(45) Date of Patent: Dec. 3, 2019

(54) METHOD FOR HIGH-SPEED PARALLEL PROCESSING FOR ULTRASONIC SIGNAL BY USING SMART DEVICE

(71) Applicants: SOGANG UNIVERSITY RESEARCH FOUNDATION, Seoul (KR); HANSONO CO. LTD., Seoul (KR)

(72) Inventors: Tai-Kyong Song, Seoul (KR); Ukyu Kong, Seoul (KR)

(73) Assignees: HANSONO CO. LTD, Seoul (KR); SOGANG UNIVERSITY RESEARCH FOUNDATION, Seoul (KR)

( * ) Notice: Subject to any disclaimer, the term of this patent is extended or adjusted under 35 U.S.C. 154(b) by 73 days.

(21) Appl. No.: 15/507,444

(22) PCT Filed: Aug. 28, 2015

(86) PCT No.: PCT/KR2015/009039
§ 371 (c)(1),
(2) Date: Jul. 20, 2017

(87) PCT Pub. No.: WO2016/032271
PCT Pub. Date: Mar. 3, 2016

(65) Prior Publication Data
US 2017/0329928 A1    Nov. 16, 2017

(30) Foreign Application Priority Data
Aug. 29, 2014  (KR) ...................... 10-2014-0114032

(51) Int. Cl.
*G06K 9/42*     (2006.01)
*G16H 50/50*    (2018.01)
(Continued)

(52) U.S. Cl.
CPC ........... *G16H 50/50* (2018.01); *A61B 8/5207* (2013.01); *G06F 9/28* (2013.01); *H04L 27/1525* (2013.01)

(58) Field of Classification Search
CPC ..... G06T 15/005; A61B 8/5207; G06F 19/00; G06F 19/321; G06F 9/28; G06F 9/3001; G16H 50/50; H04L 27/1525
See application file for complete search history.

(56) References Cited

U.S. PATENT DOCUMENTS 8,325,197 B2 * 12/2012 Won ...................... G06T 15/005
                                                              345/506
8,355,554 B2 *  1/2013 Ma ........................ A61B 6/469
                                                              382/131
(Continued)

FOREIGN PATENT DOCUMENTS

KR    1009714340000    7/2010
KR    1011325240000    5/2012
(Continued)

OTHER PUBLICATIONS

Lipchak,B. "OpenGL ES Version 3.0," The Khronos Group Inc., Aug. 6, 2012 (pp. 1-347) (Year: 2012).*

*Primary Examiner* — Bhavesh M Mehta
*Assistant Examiner* — Ian L Lemieux
(74) *Attorney, Agent, or Firm* — Duane Morris LLP; Gregory M. Lefkowitz; Jason M. Nolan

(57) ABSTRACT

The present invention relates to a method for high-speed parallel processing for an ultrasonic signal, the method used for generation of an ultrasonic image by a smart device, which is provided with a mobile graphic processing unit (GPU), by receiving an input of an ultrasonic signal. The method comprises the steps of: receiving an input of an ultrasonic signal beam-formed by means of a first rendering cycle, removing a DC component from the ultrasonic signal, (Continued)

and then separating an in-phase component and a quadrature component from the ultrasonic signal, from which the DC component has been removed, and separately outputting same; a smart device performing quadrature demodulation and envelope detection processing for the ultrasonic signal, having the in-phase component and the quadrature component, by means of a second rendering cycle; and the smart device performing scan conversion for the ultrasonic signal, which has been obtained as the result of the second rendering cycle, by means of a fifth rendering cycle, wherein the rendering cycles are formed as a graphics pipeline structure comprising a vertex shader procedure, a rasterizer procedure, and a fragment shader procedure. A method for high-speed parallel processing for an ultrasonic signal by using a smart device, according to the present invention, enables high-speed parallel processing for an ultrasonic signal by means of a mobile GPU inside a smart device even in a mobile-based environment instead of a PC-based environment, thereby enabling the providing of an image having a frame rate that is useful for medical diagnosis.

20 Claims, 10 Drawing Sheets

(51) Int. Cl.
*G06F 9/28* (2006.01)
*A61B 8/08* (2006.01)
*H04L 27/152* (2006.01)

(56) References Cited

U.S. PATENT DOCUMENTS

| | | | |
|---|---|---|---|
| 2010/0010344 A1* | 1/2010 | Ahn | A61B 8/483 600/437 |
| 2013/0063440 A1* | 3/2013 | Son | G06T 15/005 345/426 |
| 2014/0369550 A1* | 12/2014 | Davis | G06Q 30/0201 382/100 |
| 2017/0358132 A1* | 12/2017 | Munshi | G06T 1/20 |
| 2018/0101980 A1* | 4/2018 | Kwon | G06T 1/20 |
| 2019/0179589 A1* | 6/2019 | Akester | G06F 3/1431 |
| 2019/0188907 A1* | 6/2019 | Howson | G06T 11/40 |
| 2019/0213775 A1* | 7/2019 | Dimitrov | G06T 15/005 |

FOREIGN PATENT DOCUMENTS

| | | |
|---|---|---|
| KR | 1012146750000 | 12/2012 |
| KR | 1020130029149 | 3/2013 |
| KR | 1012862220000 | 7/2013 |

\* cited by examiner

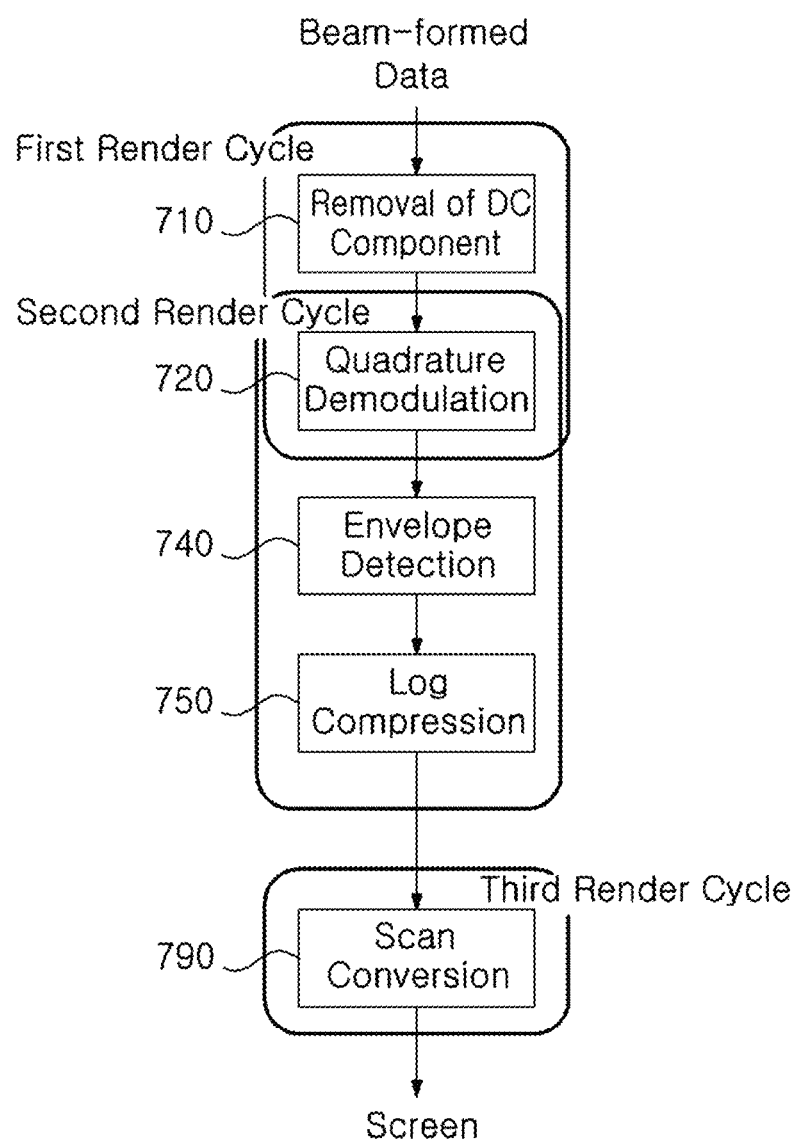

METHOD FOR HIGH-SPEED PARALLEL PROCESSING FOR ULTRASONIC SIGNAL BY USING SMART DEVICE

TECHNICAL FIELD

The present disclosure relates to a method for high-speed parallel processing for an ultrasonic signal by using a smart device, and more particularly, to a method for high-speed parallel processing for an ultrasonic signal by using a smart device, which may process and image an ultrasonic signal in a rapid and efficient way regardless of time and place by performing high-speed parallel processing to ultrasonic signals, reflected from a target, by means of a mobile GPU in a portable smart device.

BACKGROUND ART

Recently, the technologies in the medical image diagnosis field for fusing IT techniques to the medical techniques are being rapidly developed. Among them, medical ultrasonic waves mainly used in the art are useful for visualizing a tomography-scanned image in real time in order to measure size, structure and pathologic damage of muscles, sinew, internal organs, and organs of a human.

In order to implement a medical image for diagnosis by using medical ultrasonic waves as above, a probe is placed in contact with a target and an ultrasonic wave is generated therefrom, and then the ultrasonic wave reflected from the target is received to compose an image. In other words, if an ultrasonic wave is generated, the sonic wave passes through a medium within a very short time, and when the sonic wave passes between two mediums having different sonic impedances, a reflective wave is generated. At this time, the generated reflective wave is measured to reversely calculate a distance by means of the time taken until the reflected sound returns, thereby generating a medical image for diagnosis.

As medical images for diagnosis are widely used in the medical fields, many users regardless of age or sex have increasing demands to generate and check a medical image for diagnosis using an ultrasonic signal while moving regardless of time and place by means of smart devices broadly propagated. However, in spite of such demands, in case of a smart device which is portable, if an ultrasonic signal is processed using the processing power of a CPU therein, it is difficult to provide an image of a useful frame rate. In particular, even though a GPU (Graphic Processing Unit) is provided in the smart device, the parallel-processing algorithm performed in the GPU such as CUDA, OpenCL or the like under the PC-based environment cannot be equivalently performed in the environment of the smart device.

<Related Literature> KR 10-2012-0059740 (Ultrasonic system comprising one or more G, Samsung Medison) Jun. 11, 2012

DISCLOSURE

Technical Problem

The present disclosure is designed to solve the problems of the prior art, and the present disclosure is directed to providing a method for high-speed parallel processing for an ultrasonic signal by using a smart device, which may efficiently perform operations of a GPU by allowing a part of calculations allocated to a fragment shader stage in a graphics pipeline structure to be performed in a vertex shader stage having a relatively smaller amount of allocated operations, when a smart device processes an ultrasonic signal by using the graphics pipeline structure of a mobile GPU.

Technical Solution

In one general aspect, the present disclosure provides a method for high-speed parallel processing for an ultrasonic signal by using a smart device, which is used for a smart device having a mobile GPU (Graphic Processing Unit) to receive an ultrasonic signal and generate an ultrasonic image, the method comprising: by the smart device, receiving a beam-formed ultrasonic signal through a first render cycle, removing a DC component from the ultrasonic signal, and then dividing and outputting an in-phase component and a quadrature component from the ultrasonic signal free from the DC component; by the smart device, performing quadrature demodulation processing and envelope detection processing through a second render cycle to the ultrasonic signal having the in-phase component and the quadrature component; and by the smart device, performing scan conversion through a fifth render cycle to the ultrasonic signal obtained as a result of the second render cycle, wherein the render cycles has a graphics pipeline structure including a vertex shader stage, a rasterizer stage and a fragment shader stage.

In the method for high-speed parallel processing for an ultrasonic signal according to an embodiment, in the vertex shader stage, the mobile GPU may receive a plurality of vertexes, allocate a spatial region by using the received vertexes, and then calculate a spatial coordinate for the allocated spatial region to generate a calculation result in the form of a varying parameter.

In the method for high-speed parallel processing for an ultrasonic signal according to an embodiment, in the rasterizer stage, the mobile GPU may search an on-screen coordinate value corresponding to the varying parameter output in the vertex shader stage, and generate the searched coordinate value in the form of a varying parameter.

In the method for high-speed parallel processing for an ultrasonic signal according to an embodiment, in the vertex shader stage, the mobile GPU may further calculate a coordinate value located on the periphery of the on-screen coordinate value generated in the rasterizer stage, and generate a calculation result in the form of a varying parameter.

In the method for high-speed parallel processing for an ultrasonic signal according to an embodiment, in the fragment shader stage, the mobile GPU may calculate a color for the on-screen coordinate value generated in the rasterizer stage and generate a calculation result.

The method for high-speed parallel processing for an ultrasonic signal according to an embodiment may further comprise, by the mobile GPU, storing the color calculation result for the on-screen coordinate value generated in the fragment shader stage in a frame buffer.

In the method for high-speed parallel processing for an ultrasonic signal according to an embodiment, 8 to 16 varying parameters may be output depending on a specification of the mobile GPU.

In the method for high-speed parallel processing for an ultrasonic signal according to an embodiment, when an image generated in a previous render cycle is stored in a frame buffer, the mobile GPU may transfer the stored image to a texture corresponding to a memory of the mobile GPU by means of a RTT (Render To Texture) technique, and transfer the transferred image to a fragment shader stage in a graphics pipeline of a next render cycle.

In the method for high-speed parallel processing for an ultrasonic signal according to an embodiment, the mobile GPU may perform parallel processing to an ultrasonic signal by using a fixed function pipeline structure.

The method for high-speed parallel processing for an ultrasonic signal according to an embodiment may be implemented under OpenGL ES 3.0 environment.

In the method for high-speed parallel processing for an ultrasonic signal according to an embodiment, the mobile GPU may control a part of operations allocated to the fragment shader stage to be performed in advance in the vertex shader stage.

In the method for high-speed parallel processing for an ultrasonic signal according to an embodiment, in the second render cycle, the smart device may further perform decimation processing to the ultrasonic signal to which the quadrature demodulation processing is performed.

In the method for high-speed parallel processing for an ultrasonic signal according to an embodiment, in the second render cycle, the smart device may further perform log compression processing to the ultrasonic signal to which the envelope detection processing is performed.

In the method for high-speed parallel processing for an ultrasonic signal according to an embodiment, in the second render cycle, the smart device may further perform gain control processing to control an overall gain of an image with respect to the ultrasonic signal to which the log compression processing is performed.

In the method for high-speed parallel processing for an ultrasonic signal according to an embodiment, after the second render cycle is performed, the smart device may further perform removing a blackhole for the ultrasonic signal by receiving a threshold value which is regarded as a blackhole through a third render cycle and comparing sizes of the threshold value and the ultrasonic signal received in the second render cycle with each other.

In the method for high-speed parallel processing for an ultrasonic signal according to an embodiment, after the second render cycle is performed, the smart device may further perform edge enhancing through a fourth render cycle to the ultrasonic signal received in the second render cycle.

Meanwhile, there is also provided a computer-readable recording medium, on which a program for executing the method for high-speed parallel processing for an ultrasonic signal as described above with a computer is recorded.

Advantageous Effects

The method for high-speed parallel processing for an ultrasonic signal by using a smart device according to the present disclosure may provide an image of a frame rate useful for medical diagnosis by performing high-speed parallel processing to an ultrasonic signal by means of a mobile GPU in a smart device even in a mobile-based environment, other than a PC-based environment.

In addition, the method for high-speed parallel processing for an ultrasonic signal by using a smart device according to the present may distribute operations required for parallel processing of ultrasonic signals and thus process the ultrasonic signals more rapidly by allowing a part of calculations allocated to a fragment shader stage in a graphics pipeline structure to be performed in a vertex shader stage, when the ultrasonic signals are processed in parallel by using the graphics pipeline structure.

DESCRIPTION OF DRAWINGS

FIGS. 7A and 7B are diagrams showing a process of processing a render cycle, to which the present disclosure is applied for B-mode imaging.

BEST MODE

According to an optimal embodiment for implementing the present disclosure, a method for high-speed parallel processing for an ultrasonic signal by using a smart device, which is used for a smart device having a mobile GPU (Graphic Processing Unit) to receive an ultrasonic signal and generate an ultrasonic image, includes: by the smart device, receiving a beam-formed ultrasonic signal through a first render cycle, removing a DC component from the ultrasonic signal, and then dividing and outputting an in-phase component and a quadrature component from the ultrasonic signal free from the DC component; performing quadrature demodulation processing and envelope detection processing through a second render cycle to the ultrasonic signal having the in-phase component and the quadrature component; and performing scan conversion through a fifth render cycle to the ultrasonic signal obtained as a result of the second render cycle, wherein the render cycles has a graphics pipeline structure including a vertex shader stage, a rasterizer stage and a fragment shader stage.

MODE FOR INVENTION

Hereinafter, the present disclosure will be described in detail so as to be easily implemented by those having ordinary skill in the art with reference to the preferred embodiments and the accompanying drawings. However, the present disclosure can be implemented in various ways without being limited to these embodiments.

First, the structure of a render cycle to which the present disclosure is applied will be described in brief with reference to FIG. 1.

A unit for generating a single image in the OpenGL ES environment where the present disclosure is implemented is called a render cycle.

Figure 1:
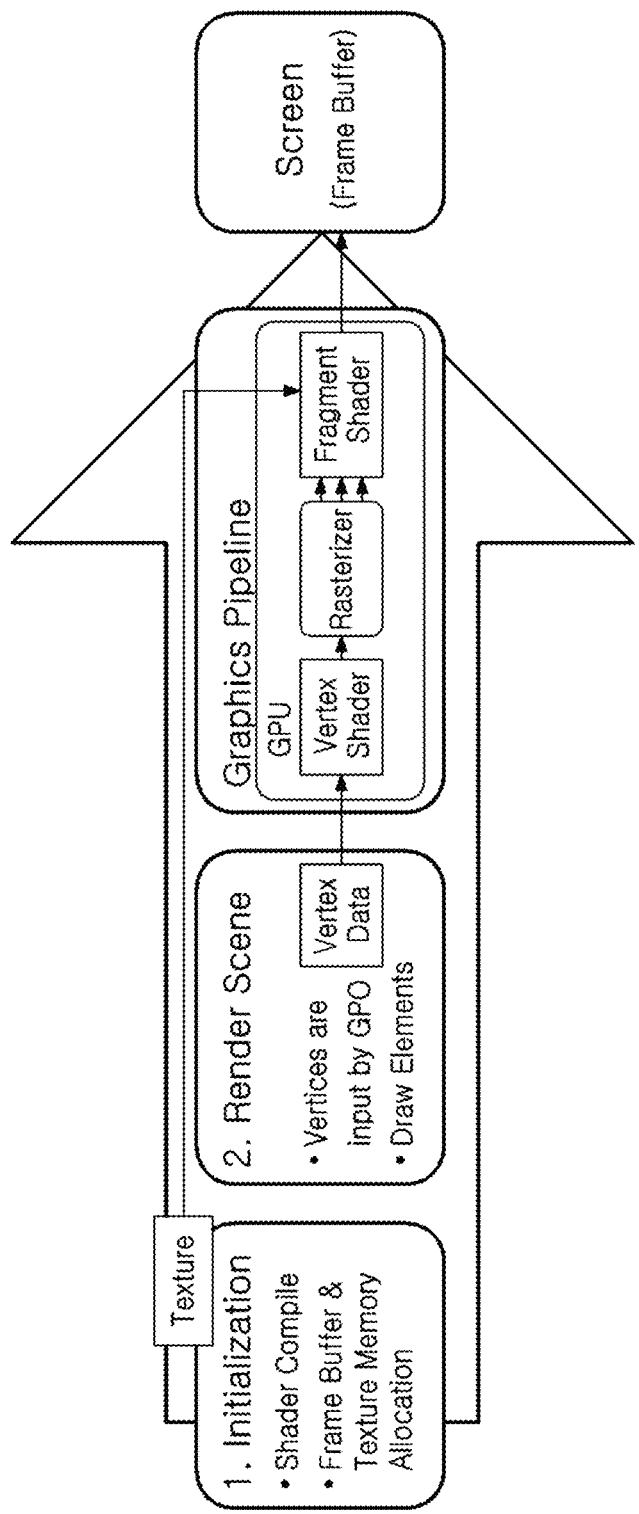
FIG. 1 is a diagram for illustrating a process of processing a single render cycle.

FIG. 1 is a diagram for illustrating a process of processing a single render cycle.

As shown in FIG. 1, in the render cycle, an initialization process, a render scene process and a graphics pipeline process are performed to beam-formed data to generate an ultrasonic image.

First, in the initialization process, a vertex shader stage and a fragment shader stage in a graphics pipeline structure, which are programmable by a user, are compiled, attribute and size of a texture serving as a memory in a GPU (Graphic Processing Unit) storing input data are set, and attribute and size of a frame buffer storing a resultant output image of the render cycle are set.

In the following render scene process, vertices to be used for allocating a spatial region having an image are input to a following graphics pipeline structure, and an instruction for initiating the graphics pipeline is provided by using a command such as glDrawElements.

The graphics pipeline process is performed using the GPU and substantially occupies most of calculations of the GPU.

Hereinafter, the graphics pipeline structure performing actual calculations will be described in detail with reference to FIG. 2.

Figure 2:
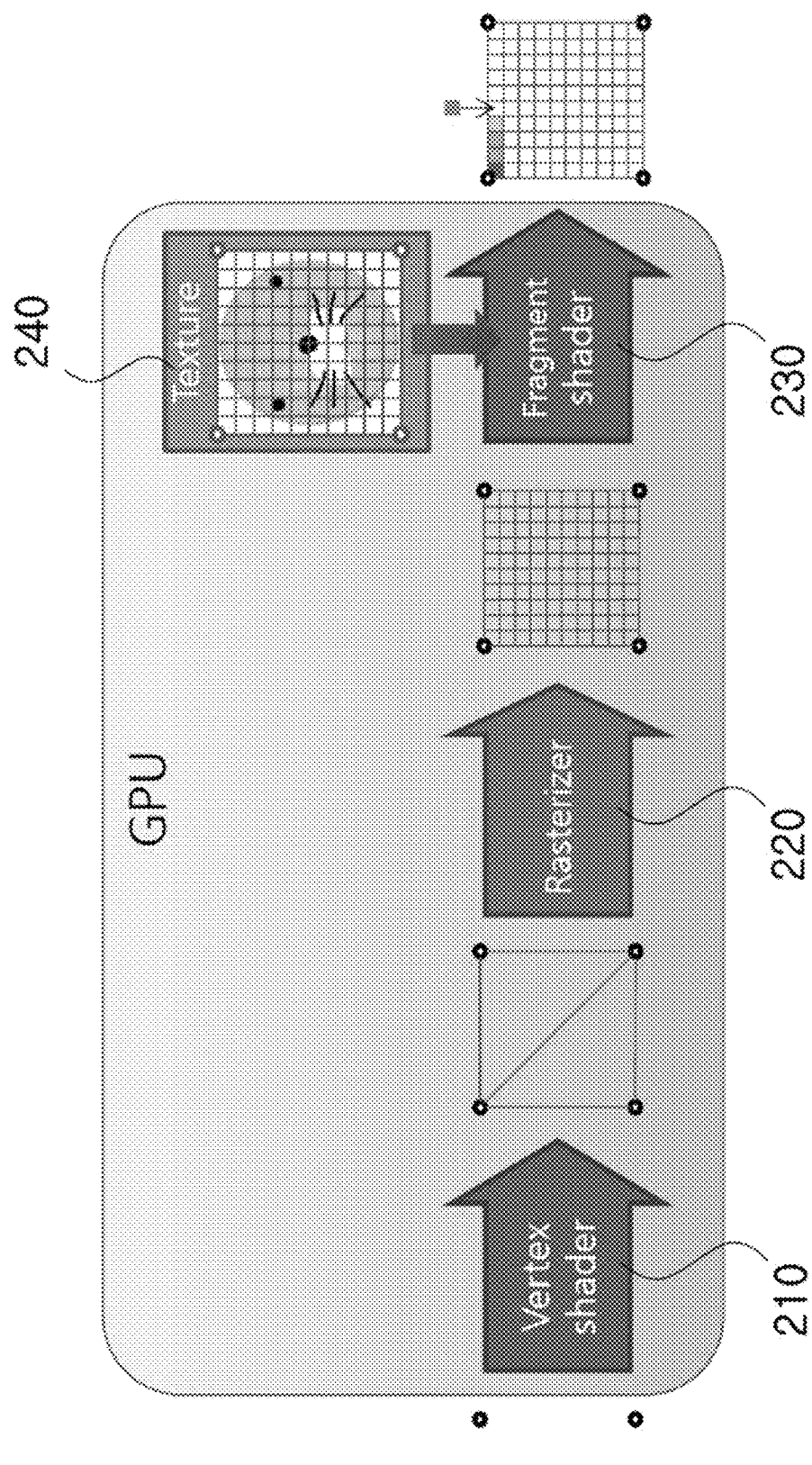
FIG. 2 is a diagram for illustrating a calculating process in graphics pipeline structure of a render cycle.

FIG. 2 is a diagram for illustrating a calculating process in a graphics pipeline structure of a render cycle, which may be implemented in a smart device having a mobile GPU (Graphic Processing Unit).

As shown in FIG. 2, a graphics pipeline under the OpenGL ES 3.0 environment includes a vertex shader stage 210, a rasterizer stage 220, a fragment shader stage 230 and a texture stage 240.

In the vertex shader stage 210, spatial coordinates of the vertices input in the render scene process are calculated. Subsequently, in the rasterizer stage 220, coordinates of pixels on a screen, present within the space allocated in the vertex shader stage 210, are calculated and output. After that, in the fragment shader stage 230, the coordinates of the pixels output in the rasterizer stage 220 are received and colors of the corresponding pixels are calculated. At this time, when colors of the pixels are calculated in the fragment shader stage 230, an image previously uploaded to a texture serving as a GPU memory may be loaded and used.

Among the stages of the graphics pipeline structure, the vertex shader stage 210 and the fragment shader stage 230 are programmable by a user. By programming a shader which determines operations of the vertex shader stage and the fragment shader stage, it is possible to give a command to produce a graphic intended by a programmer at the GPU. The result generated at the graphics pipeline is stored in a frame buffer.

A series of the above processes is a procedure of a single render cycle for generating a single image. In addition, a method for receiving an image generated through a single render cycle as an input and performing another calculation is called a RTT (Render to Texture) technique.

Hereinafter, a process of processing two render cycles by applying the RTT technique will be described.

Figure 3:
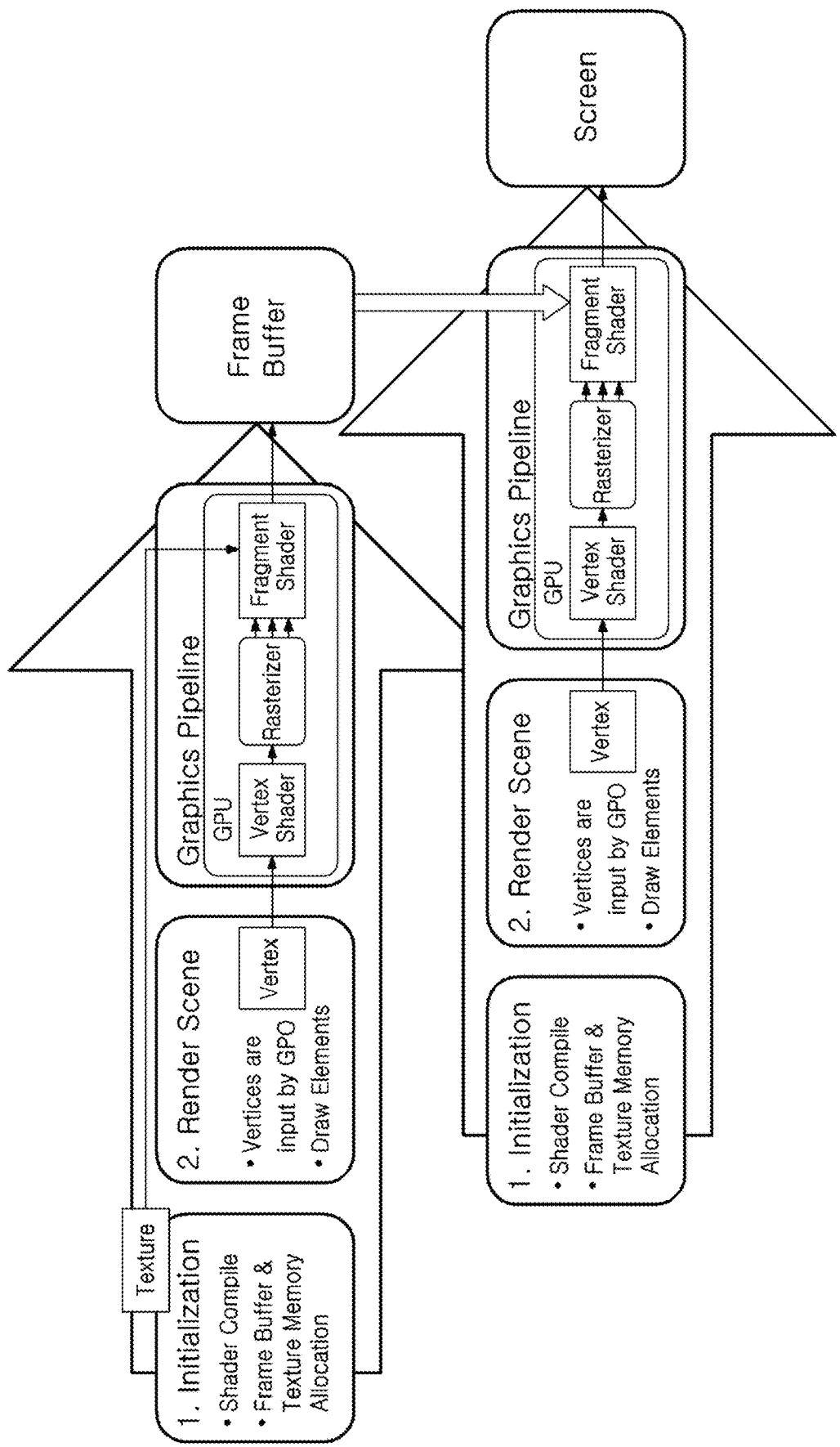
FIG. 3 is a diagram for illustrating a process of processing two render cycles.

FIG. 3 is a diagram for illustrating a process of processing two render cycles.

The resultant product of the first render cycle described above with reference to FIG. 2 is stored in the frame buffer, and this is rendered using a texture and used again as an input of a next render cycle.

Hereinafter, an example of ultrasonic signal processing using the present disclosure will be described.

First, in order to allow data used at the graphics pipeline to be used at the GPU as frame-based data at a main memory of a smart device, the mobile CPU of the smart device uploads the data to the texture serving as a memory of the GPU. At the initialization process which is a first process of the render cycle, the GPU allocates a frame buffer and a texture memory, and at this time, the attribute of the texture memory may be defined differently depending on the kind of input data. For example, if beam-formed RF data in the form of 16-bit integer is received and processed, the texture storing the data to be input as a function is defined using glTexImage2D (GL_TEXTURE_2D, 0, GL_RED, sample_no, scanline_no, 0, GL_RED_INTEGER, GL_SHORT, inputData). At this time, since the input data is frame-based data, the glTexImage2D function is used to define a 2D texture, and also since the data is 16-bit integer data, GL_R16I meaning that the 16-bit integer data is stored at a portion corresponding to a red color is used. In addition, the number of samples in an axial direction of the frame data is input to sample_no, and the number of scan lines of the frame data is input to scanline_no to input the size information of the frame data. In addition, GL_RED means that only a red color is used at GL_R16I, and GL_RED_INTEGER followed means that the kind of data is integer. inputData at a last portion is a pointer indicating the input data.

Subsequently, when beam-forming is performed to the data, data showing a location where fine delay is applied is loaded, or when scan conversion is performed, it is necessary to perform bilinear interpolation. In the OpenGL ES 3.0 environment where the present disclosure is applied, bilinear interpolation is not performed for shader programming by using the characteristics of the texture, but a result of the bilinear interpolation may be loaded when data showing a location other than the coordinate of an integer of the texture is loaded. In the initialization stage which is a first stage of the render cycle, sizes of the frame buffer and the texture memory are allocated, and here, the attribute of the texture is designated.

In particular, when a coordinate access is loaded at the shader for the texture using a glTexParameteri function expressed as below, it may be determined whether the coordinate access is loaded by performing bilinear interpolation or a value closest thereto is loaded.

glTexParameteri (GL_TEXTURE_2D, GL_TEXTURE_MAG_FILTER, GL_NEAREST);
glTexParameteri (GL_TEXTURE_2D, GL_TEXTURE_MIN_FILTER, GL_LINEAR);

At this time, GL_TEXTURE_MAG_FILTER represents a case where the texture is output in an enlarged state over the original size, and GL_NEAREST represents that, when the texture is enlarged over the original size, portions not filled by the original size of the texture are filled with a closest value. If this portion is expressed using GL_LINEAR, the screen is filled with the results obtained by performing the bilinear interpolation. In addition, GL_TEXTURE_MIN_FILTER represents a case where the texture is output on the screen in a reduced state than the original size, GL_NEAREST represents that the screen is filled with a value of the texture closest to the coordinate which approaches when the screen is filled with original values of the texture, and GL_LINEAR represents that the screen is filled by means of bilinear interpolation.

Through the above process, the result of a single render cycle is stored in the frame buffer. In addition, as necessary, the result stored in the frame buffer may be used as an input of a next render cycle followed by using the RTT (Render to Texture) technique. In the initialization stage which is a first process of the render cycle, the frame buffer and the texture memory are allocated, and here the attribute of the frame buffer configured to store an output of the graphic pipeline is defined differently depending on the kind of the output. For example, when an In-phase component and a quadrature component are output by performing quadrature demodulation, the attribute of the frame buffer may be defined as follows to store the In-phase component and the quadrature component.

glTexImage2D (GL_TEXTURE_2D, 0, GL_RG16F, sample_no, scanline_no, 0, GL_RG, GL_FLOAT, 0);

At this time, since the input data is frame-based data, the mobile GPU uses a glTexImage2D function to define a 2D texture, and while the output In-phase component and the output quadrature component are being stored, they are stored as 16-bit float to enhance the accuracy in calculation, and also GL_RG16F is used to store the In-phase component and the quadrature component at red and green locations, respectively. In addition, the mobile GPU inputs the number of samples in an axial direction of the frame data to sample_no, and inputs the number of scan lines of the frame data to scanline_no to input size information of the frame data. GL_RG means that the In-phase component and the quadrature component are stored at red and green locations of each pixel as in GL_RG16F above, and GL_FLOAT followed means that the data has a floating size. At a last location of the glTexImage2D function, a pointer of the data input when defining an initially input texture is placed, but when defining a frame buffer for using the RTT technique, 0 is input thereto which means that the corresponding frame buffer remains empty, and a pointer indicating the data input at this time is placed.

At the render scene stage which is a second stage of the render cycle, the mobile GPU gives a command for entering the graphics pipeline and also a command for designating a frame buffer to which the graphics pipeline is to be stored.

In the graphics pipeline of OpenGL ES 3.0, coordinates of pixels present in a spatial region determined in the vertex shader stage are regarded as having a size of the frame buffer which stores an output of the graphics pipeline structure, and are thus searched at the rasterizer stage. Therefore, decimation signal processing may be performed by setting the size of the frame buffer serving as a texture which is a rendering target at the RTT technique to be smaller than the size of the texture input to the graphics pipeline. For example, if beam-formed data having 128 scan lines with 4096 samples in an axial direction is input and decimation is performed in an axial direction as much as a ratio 2, the texture which is to store the input beam-formed data is uploaded to a texture having a width of 4096 and a height of 128 so as to be loaded at the fragment shader, and the attribute of the frame buffer which is to store the output of the graphics pipeline is set to have a width of 2048 and a height of 128. Accordingly, at the rasterizer stage, screen coordinates of every other pixel in an axial direction are searched at the input texture and provided to the fragment shader stage. At the fragment shader stage, the coordinates searched at the rasterizer stage are received and the data at the coordinates of every other pixel in the input texture in an axial direction is loaded.

In another example, if beam-formed data having 2854 samples in an axial directions and 192 scan lines is received and decimation is performed in an axial direction as much as a ratio 2, the texture which is to store the input beam-formed data is uploaded to a texture having a width of 2,854 and a height of 192 so as to be loaded at the fragment shader, and the frame buffer which is to store the output of the graphics pipeline is set to have an attribute with a width of 1,427 and a height of 192.

In particular, the mobile GPU has two pipeline structures, and a first pipeline structure is a fixed function pipeline, where physical processing units used for calculations at the vertex shader stage and the fragment shader stage are separately allocated. A second pipeline structure is a unified shader model, where physical processing units used for calculations at the vertex shader stage and the fragment shader stage are integrated into a single unit, so that the processing unit is allocated to calculation of each shader stage according to the necessity for calculation at the vertex shader stage and the fragment shader stage depending on the operation performed by a user by means of shader programming. The mobile GPU having a fixed function pipeline structure includes Mali-400 series, manufactured by ARM, Adreno 130, manufactured by Qualcomm, or the like. Also, the mobile GPU having a unified shader model structure includes Mali-T600 series, manufactured by ARM, Adreno 200 series, Adreno 300 series, Adreno 400 series, manufactured by Qualcomm, or the like. The structure of such a mobile GPU tends to change from the fixed function pipeline structure to the unified shader model.

An optimization method for sharing loads between the vertex shader stage and the fragment shader stage according to the present disclosure may give an effect when being applied to a smart device whose mobile GPU has a fixed function pipeline structure.

The ultrasonic signal processing using the graphics pipeline under an OpenGL ES 3.0 environment is implemented by means of shader programming which determines operations of the vertex shader stage and the fragment shader stage which are programmable by a user. In particular, since both input data and output data have a rectangular shape, at the vertex shader stage, other operations are not performed than an operation of allocating a rectangular region by using only four vertices, and most operations are performed at the fragment shader stage. Therefore, if a mobile GPU having a fixed function pipeline structure where the number of processing units allocated to calculations of the vertex shader stage and the fragment shader stage is not floating according to shader programming, different from the unified shader model, is used, a portion of the calculations allocated to the fragment shader stage during shader programming is performed at the vertex shader stage, and thus the calculation speed of the ultrasonic signal may be enhanced by using a processing unit which is allocated to calculations of the vertex shader stage which is not in use.

Hereinafter, a calculation process of the vertex shader stage and the fragment shader will be described in detail with reference to FIG. 4.

Figure 4:
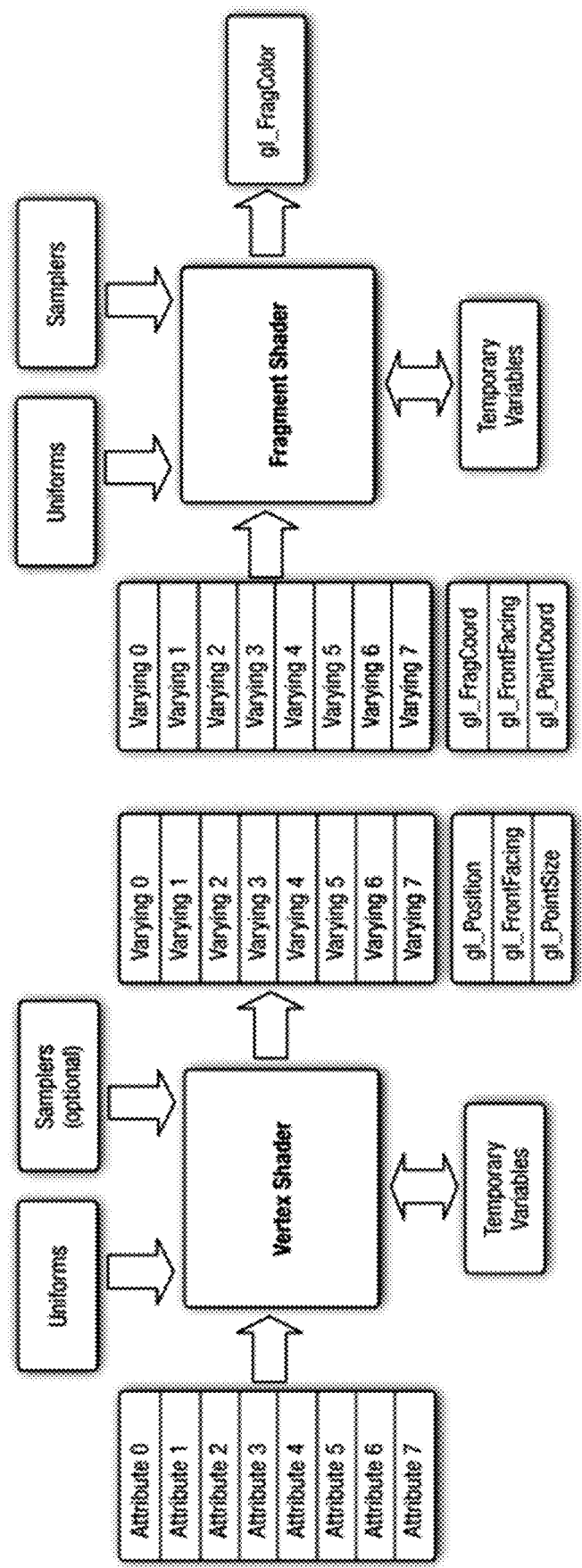
FIG. 4 is a block diagram showing a vertex shader stage and a fragment shader stage.

FIG. 4 is a block diagram showing a vertex shader stage and a fragment shader stage.

As shown in FIG. 4, first, the calculation result obtained at the vertex shader stage is output as a varying parameter, and the output value is input to the fragment shader stage in the form of a varying parameter by searching values present on the screen through the rasterizer stage. For example, the calculation result obtained at the vertex shader stage is generally a coordinate representing a spatial region, and at this time, if the coordinate value is output as a varying parameter, coordinates of pixels within the spatial region defined at the vertex shader stage on the screen suitable for the size of the screen of the corresponding render cycle, namely the frame buffer serving as a rendering target, are input as varying parameters of the fragment shader stage.

Subsequently, at the fragment shader stage, the input data uploaded to the texture are accessed using the coordinates obtained as a single varying parameter and used for calculation.

If a filtering calculation is included in the render cycle processing procedure and thus it is needed to access texture data as much as the number of tabs in the filter in order to calculate a value of a single pixel at the fragment shader stage, at the fragment shader stage, an adjacent coordinate of the texture should be calculated by making an addition to a single coordinate input in the form of a varying parameter and the adjacent coordinate should be loaded at the texture. However, seeing the structure of the shader depicted in FIG. 4, it is possible to use at least 8 varying parameters and at most 16 varying parameters depending on the specification of the GPU. In other words, if the mobile GPU calculates a value corresponding to an adjacent coordinate at the vertex shader stage in advance and transfers the calculation result as at most 16 varying parameters to the fragment shader stage, it is possible to exclude a process for calculating an adjacent coordinate at the fragment shader stage. However, if the number of tabs at the filter exceeds 16, it may be still needed to calculate an adjacent coordinate at the fragment shader stage. Nevertheless, at the fragment shader stage, a smaller number of coordinates is calculated in comparison to the previous case.

In addition, it may be understood that if bilinear interpolation is required at the ultrasonic signal processing procedure even at the bilinear interpolation method using characteristics of OpenGL ES 3.0 Texture described above, bilinear interpolation may be performed instantly using the characteristics of the OpenGI ES 3.0 texture without any separate programming for the bilinear interpolation. However, there is a difference in operation rates between the case where bilinear interpolation is performed by setting the attribute of the texture as GL_LINEAR and the case where an adjacent value is obtained by setting the attribute as GL_NEAREST. Therefore, if data is loaded only at an integer coordinate of the texture without bilinear interpolation, it is possible to enhance the calculation rate by setting the attribute of the texture as GL_NEAREST.

Hereinafter, a process of uploading data with a size having more than 4096 samples in an axial direction to the data will be described.

In a mobile GPU commercially used at the present, the size, width and height of a texture are limited to 4096 pixels, respectively. Therefore, in the existing method as described above, it is impossible to upload ultrasonic signal data with a size having more than 4096 samples in an axial direction to the texture so that the data can be loaded and used at the shader stage.

Since the height and size are limited to 4096 pixels, if the texture is defined as GL_RGBA at the initialization process, at a single pixel, ultrasonic data may be input to red, green, blue and alpha sites one by one, which ensures four kinds of information to be stored. In other words, in an axial direction, data of 16,384 (4096×4) samples may be input in an axial direction to the maximum.

Figure 5:
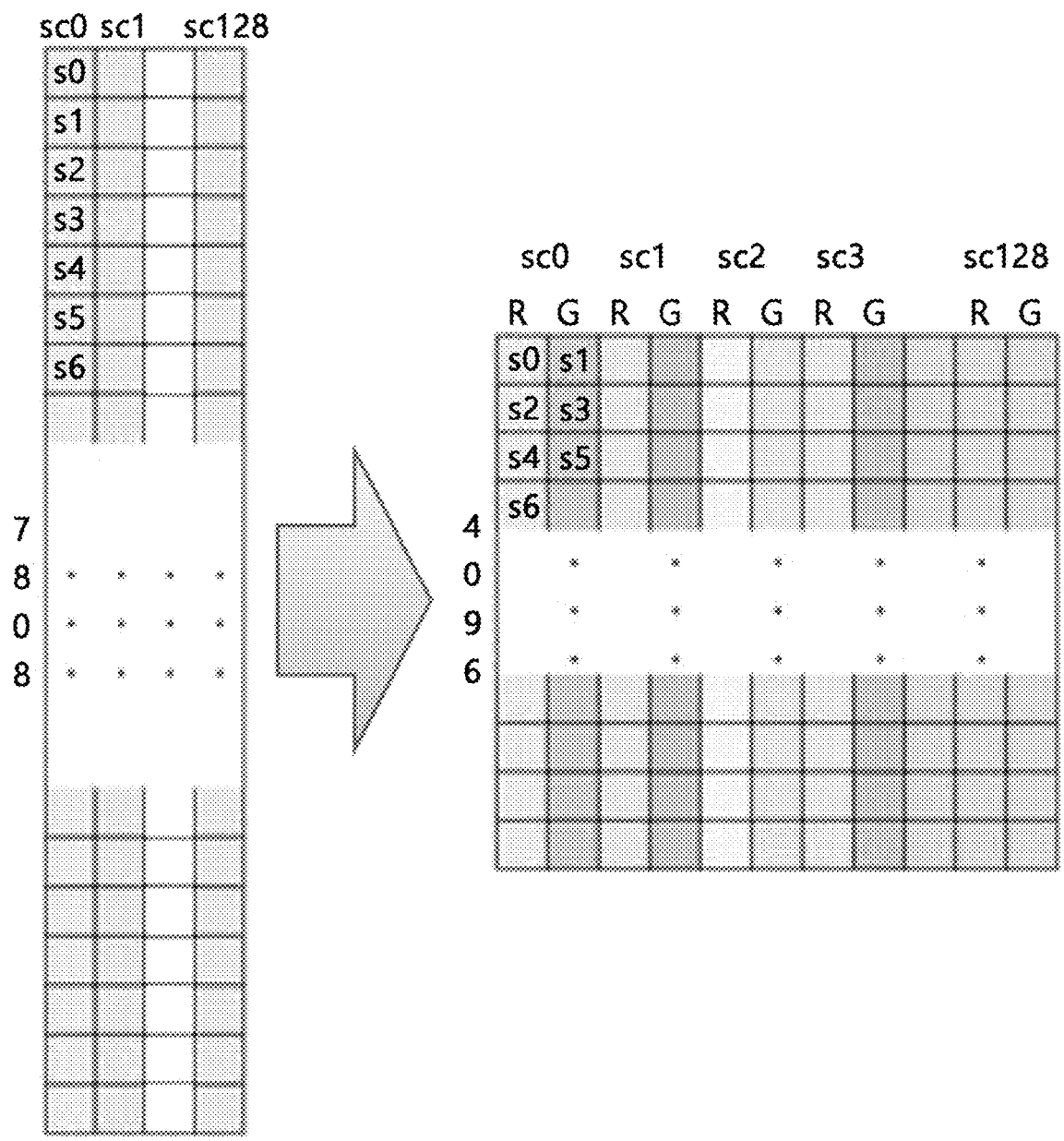
FIG. 5 is a diagram showing a process of uploading data of a size having 4096 samples in an axial direction to a texture.

FIG. 5 is a diagram showing a process of uploading data of a size having more than 4096 samples in an axial direction to a texture.

As shown in FIG. 5, ultrasonic data having 7808 samples in an axial direction and having 128 samples in a lateral direction are uploaded to the texture.

For example, assuming that data are set as s0, s1, . . . in order from the top in an axial direction where the number of scan line is 0 (sc0), the attribute of the texture is designated as GL_RG16I so that s0, s2, s4, s7806, s7808 which are 16-bit integers are stored at red sites and s1, s3, s5, s7807 are stored at green sites. The ultrasonic signal data are also stored identically in the other scan lines. At the fragment shader stage, in order to use the ultrasonic signal data stored as above, pixel data of a coordinate transferred at the rasterizer stage are loaded, and then data at a necessary location among the red and green sites is selectively used.

Hereinafter, a process for performing B-mode imaging by using the method for high-speed parallel processing for an ultrasonic signal by using a smart device according to the present disclosure will be described in detail.

First, a device used for implementing this embodiment is Google new Nexus7 (2013), in which OS is Android 4.4.2 KitKat, Snapdragon S4 pro AP of Qualcomm is loaded, and Adreno 320 is loaded as a mobile GPU. In addition, the development environment of this embodiment uses Eclipse 4.2.1, and Android NDK r9c version is used to allow linkages with JAVA native language (C++) in developing Android applications.

Figure 6:
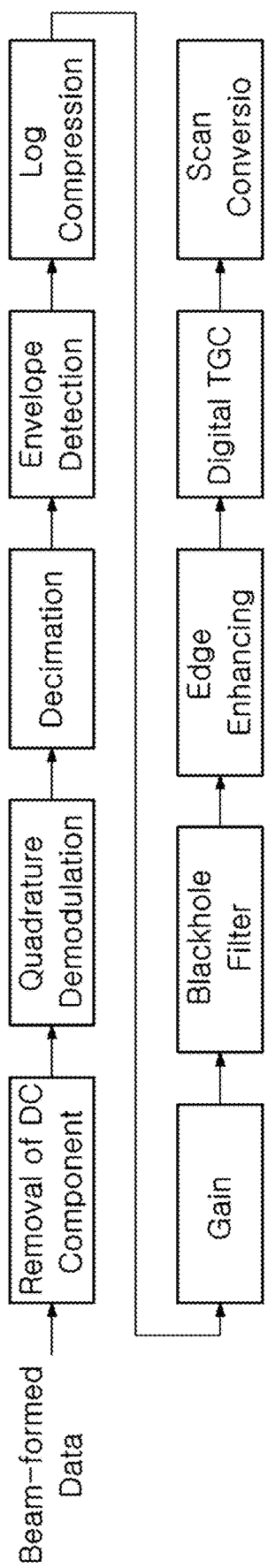
FIG. 6 is a diagram showing a signal path for B-mode imaging.

FIG. 6 is a diagram showing a signal path for B-mode imaging.

The input data used in FIG. 6 is beam-formed data having 2854 samples in an axial direction and 192 scan lines, with a central frequency of 3.3 MHz, which is obtained at a sampling rate of 20 MHz. The signal path represents a general B-mode imaging process. After a DC component is removed from the input data as described above, a time gain compensator (TGC) is performed, subsequently decimation is performed with quadrature demodulation and ratio 2, and envelope detection and log compression are performed. After that, gain control capable of adjusting an overall gain of an image, blackhole filtering, edge enhancing and digital scan conversion (DSC) are performed successively.

Figure 7A:
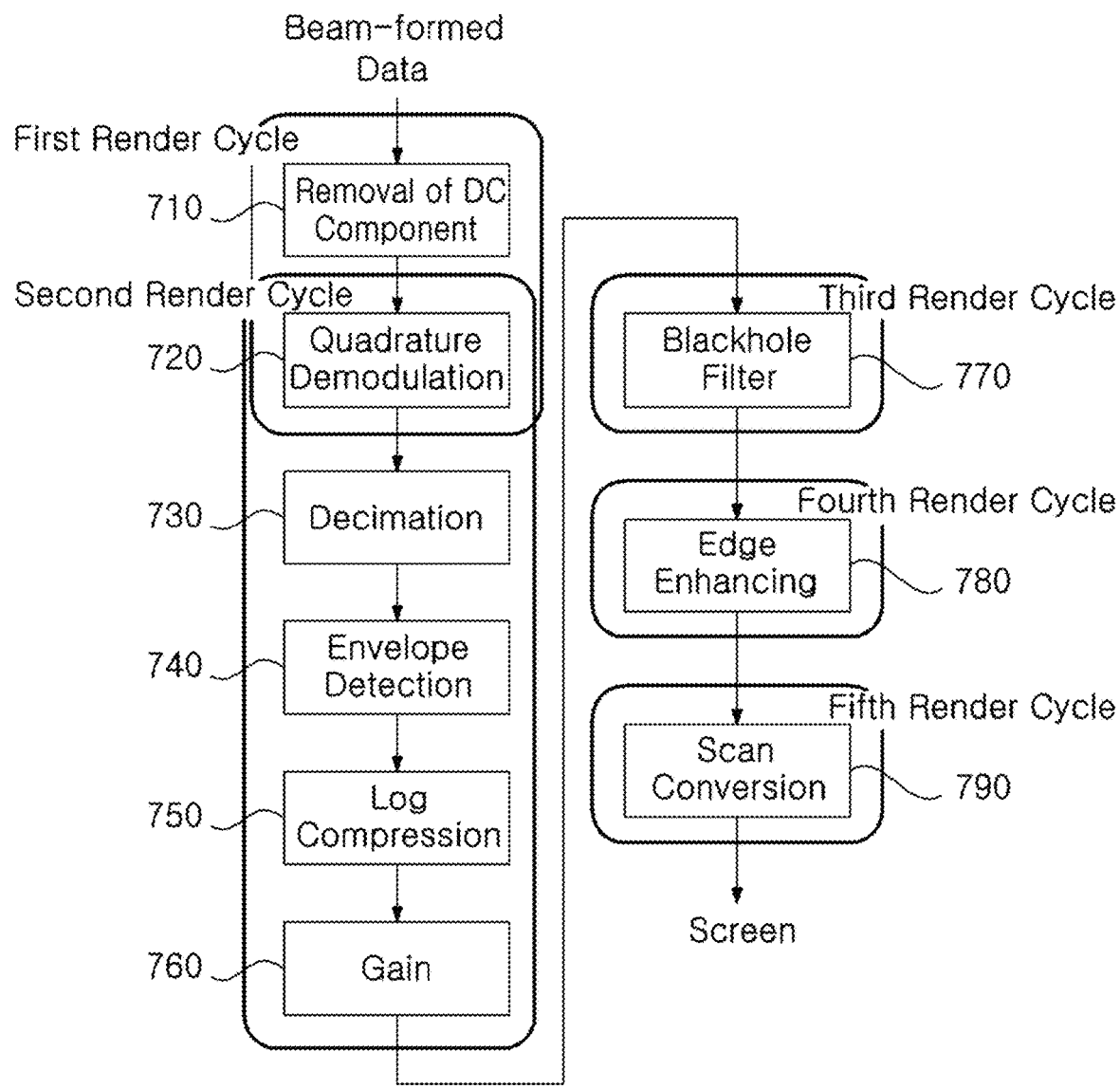

A render cycle for implementing the signal path for B-mode imaging with OpenGL ES 3.0 is depicted in FIGS. 7A and 7B.

FIG. 7A is a diagram showing a render cycle processing procedure to which the present disclosure is applied for B-mode imaging.

First, the signal path is divided into another render cycle if a calculation result of a single signal block is already completed to be processed at another signal block. For example, if a former signal block is performed and then several tabs are being filtered at a next signal block, in order to obtain a value of a pixel to be calculated at the present by the graphics pipeline implemented by means of the GPU, neighboring values are also required along with a texture value corresponding to a coordinate of a current pixel. Therefore, in order to access neighboring values together, calculation results of the neighboring values should be prepared already, and thus the render cycle is divided to store the calculation result of the former signal block in the frame buffer based on frames and then is textured by means of the RTT technique to be used as an input at the next render cycle.

In addition, since the calculation processes in a single render cycle are performed simultaneously, it is advantageous for improving the performance to set the number of render cycles to the minimum. At this time, the calculations performed at the render cycle may be performed as much as the number of pixels stored on the buffer at which the output result is to be stored.

In each render cycle divided based on the above criterion, a first render cycle will be described in detail.

At the first render cycle, a DC component is removed from the beam-formed data, and a part of the quadrature demodulation process is performed to output data (x_i, x_q). At this time, a DC component removing signal block 710 for removing the DC component includes a 32-tab Hilbert filter, and high band pass filtering is performed using the filter to remove the DC component from the beam-formed data.

Figure 8:
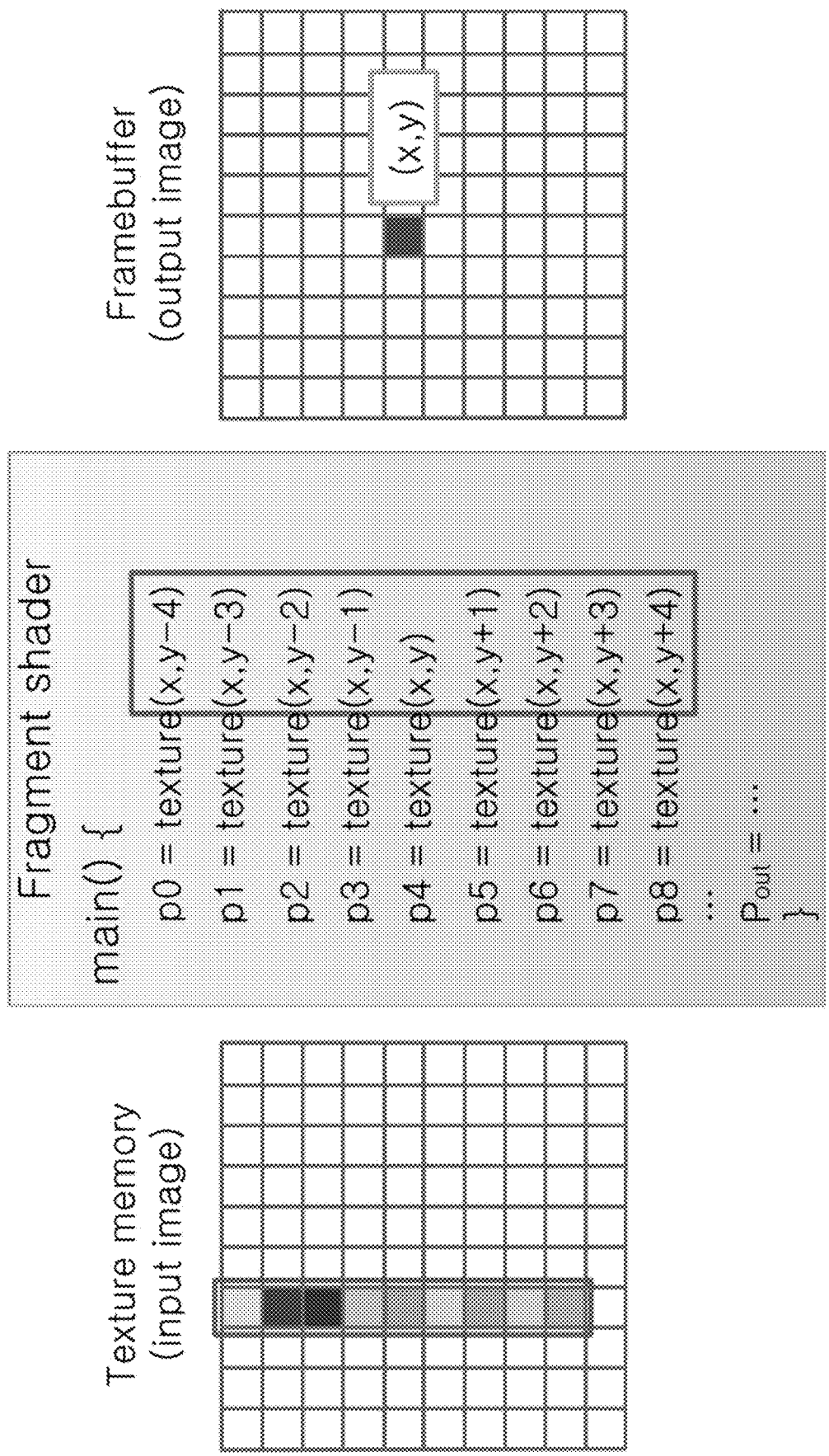
FIG. 8 is a diagram for illustrating a 9-tab filtering process in the graphics pipeline.
Figure 9:
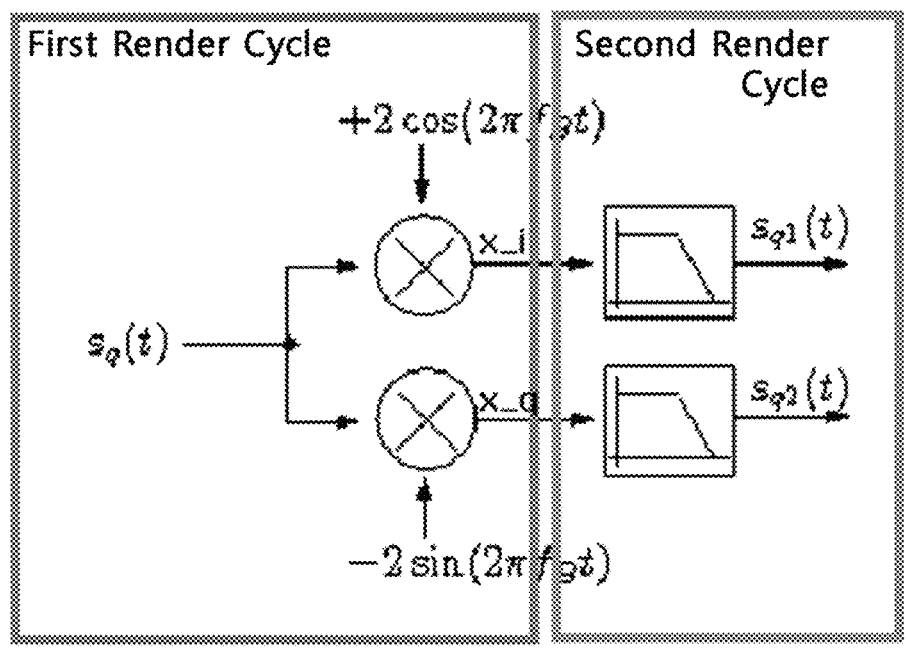
FIG. 9 is a diagram for illustrating an example of an ultrasonic signal processing procedure between a first render cycle and a second render cycle.

FIG. 8 is a diagram for illustrating a 9-tab filtering process in the graphics pipeline.

As shown in FIG. 8, at the fragment shader stage, a main function ( ) of the fragment shader stage is performed repeatedly as much as the number of pixels present in the frame buffer. Whenever the main function ( ) is performed once, a color of the corresponding pixel coordinate of the frame buffer is determined. Therefore, when filtering is performed, data of a neighboring coordinate on the texture (the input image) corresponding to a pixel coordinate of the frame buffer, which is currently being calculated, is required in a single main function ( ). Therefore, seeing FIG. 8 in detail, if a coordinate of a pixel currently calculated is (x, y), values of p0-p8 are loaded as a texture function ( ) as neighboring data on the texture by calculating values on the y axis. After that, filter coefficient and convolusion of the loaded p0-p8 are performed, and the result is output to Pout and stored at a corresponding coordinate on the frame buffer. In addition, in order to calculate a value of a next pixel, the main function ( ) is repeatedly performed based on a next coordinate of the frame buffer. In the same way, the main function ( ) is repeatedly performed as much as the number of pixels present in the frame buffer, and the filtering result is stored in the frame buffer based on frames. In this way, in the embodiment of B-mode imaging, 16-tab high band pass filtering is performed.

After that, signal processing is performed at the first render cycle until a quadrature demodulation signal block 720 multiplies cos and sin and outputs an in-phase component and a quadrature component. Since the first render cycle has two outputs, namely an in-phase component and a quadrature component, the frame buffer where the output of the first render cycle is stored is set as GL_RG16F so that the in-phase component is stored at a red site and the quadrature component is stored at a green site. The size of the frame buffer is identical to that of the input. When the output data of the first render cycle is transferred to a second render cycle, the data is stored in the frame buffer as a 16-bit floating form in order to maintain accuracy in calculation.

In other words, at the first render cycle, beam-formed data having a pixel size of 2854×192 is input, and after calculations in the number of 2854×192=547,968, output data x_i, x_q having 2854×192 pixels are output.

Subsequently, at the second render cycle, the in-phase component and the quadrature component stored in the frame buffer at the first render cycle are received as input texture by means of the RTT technique, and decimation signal processing 730 is performed. Since a decimation ratio is 2, the frame buffer where the result of the second render cycle is to be stored is set to have a width of 1427 which is a half of 2854. In addition, since the low band pass filtering is required in duplicate at the quadrature demodulation process 720 and the decimation process 730, the filter is designed so that the low band pass filtering may be performed at the same time at every process. Therefore, low band pass filtering is performed to the input data, envelope detection is performed using a square-root and then log compression is performed, and finally a gain is multiplied to control a gain of the entire image. The result of the second render cycle passes through the envelope detection process 740 to compose the components into a single component, and thus the frame buffer where the output data is to be stored is stored at a red site as 16-bit floating by means of GL_R16F.

In other words, at the second render cycle, the data (x_i, x_q) having a pixel size of 2854×192 output at the former first render cycle is input, and the quadrature demodulation process 720 is performed. An anti-aliasing filter (LPF) put after the quadrature demodulation process 720 and before the decimation process 730 is performed once between quadrature demodulation and decimation. Subsequently, envelope component detection 740 is performed to the input data by using a square-root, and a scale is matched by means of the log compression process 750. Finally, an overall gain 760 is multiplied to control an overall gain to output log compression data having a pixel size of 1427×192. At this time, in order to output the log compression data, operations are performed in the number of 1427×192=273,984 in total.

At the third render cycle, blackhole filtering 770 is performed using a 3×3 averaging filter. In order to set the degree of averaging, a threshold value representing a corresponding pixel value as blackhole is input from a user, and the averaged result is output only when a value located at the center of a window of threshold value 3×3 is equal to or smaller than the threshold value, and the value located at the existing center is output in other cases. At this time, since the 3×3 averaging filter also needs a value of a neighboring coordinate in order to calculate a value of a pixel, this should be performed after all calculations of a former render cycle are completed, and thus the render cycle is divided.

In other words, at the third render cycle, the log compression data having a pixel size of 1427×192 output at the former second render cycle is input, and 3×3 averaging filtering is performed to the input log compression data to remove blackhole, and accordingly the blackhole having a pixel size of 1427×192 outputs filtered data (or, blackhole filtered data). At this time, the number of calculations performed for the blackhole to output the filtered data is 1427×192=273,984 in total.

After that, at the fourth render cycle, edge enhancing 780 is performed by detecting a contour of the data by using a 3×3 Sobel filter. Edge enhancing is performed by adding an image where an edge component is detected by means of the Sobel filtering to an existing image, and a weight representing the degree of adding the detected edge component image is input from a user to set the intensity of enhancing. In particular, since the 3×3 Sobel filter also needs a value of a neighboring coordinate in order to calculate a value of a pixel, this should be performed after all calculations of a former render cycle are completed, and thus the render cycle is divided.

In other words, at the fourth render cycle, the data free from blackhole (blackhole filtered data) having a pixel size of 1427×192 output at the third render cycle is input, and 3×3 Sobel filtering is performed to detect an edge component for edge enhancing, so that edge enhanced having a pixel size of 1427×192 is output. At this time, the number of calculations performed for outputting the edge enhanced data is 1427×192=273,984 in total.

Subsequently, at the fifth render cycle, scan conversion 790 is performed. The data used in this embodiment is data obtained from a convex probe, and thus convex scan conversion is performed. At this time, the render cycle is divided for the scan conversion even though a value of a neighboring coordinate is not required, like the filtering process, because the number of calculations in a single render cycle is proportional to the number of pixels of a rendering target. Therefore, the output of the scan conversion includes 830 pixels in width and 640 pixels in height, and thus assuming that an amount of calculations required for a single pixel is a, the number of required calculations is 830×640×α (531200α) in total.

In other words, at the fifth render cycle, the edge enhanced data having a pixel size of 1427×192 output at the former fourth render cycle is input, and digital scan conversion is performed to the input data to generate and output a final output image (or, a digital scan conversed image) having a pixel size of 830×640. At this time, the number of calculations is 830×640=531,200.

Meanwhile, at the fourth render cycle, calculations are required in the number of 1427×192×α (273984α). If the render cycle is not divided but calculations are performed in a single render cycle, all calculations are performed simultaneously in a single render cycle, and thus Sobel filtering is performed more than required. However, this problem is prevented in the present disclosure.

Therefore, in order to reduce unnecessary calculations, it is important to divide the render cycle in consideration of the number of pixels of the out frame buffer.

FIG. 7B is a diagram showing each render cycle which is reconfigured just with minimal calculations required for processing an ultrasonic signal in FIG. 7A which shows a render cycle processing procedure. In more detail, at the second render cycle of FIG. 7A, the decimation process 730 and the gain control process 760 are excluded, also the blackhole filtering process 770 included in the third render cycle of FIG. 7A is excluded, and finally the edge enhancing process 780 included in the fourth render cycle of FIG. 7A is excluded. Therefore, as a result, the render cycles are reduced to 3 render cycles as a whole and reconfigured as shown in FIG. 7B. In other words, the quadrature demodulation process 720 and the envelope detection process 740 of the reconfigured second render cycle may be bound in a single render cycle in view of 'demodulation'.

A series of processes may also be implemented by separate render cycles, but it is desirable to minimize the number of render cycles as small as possible for enhancing the performance. Since the number of OpenGL ES API performed by the master CPU increases at the initialization stage of FIG. 3 and also data are moved between the render cycles, time is consumed additionally. Therefore, it is desirable in view of calculation speed to minimize the number of render cycles. However, if a signal processing block including a filtering calculation is performed at the same render cycle as a former signal processing block, calculations are performed in duplicate. This is because the calculation of the former signal processing block should be performed to neighboring data required for filtering whenever a calculation point is filtered. A render cycle optimized in consideration of this corresponds to FIG. 7B. Meanwhile, the processes excluded in FIG. 7B may be selectively added if they are required for implementation.

Figure 10:
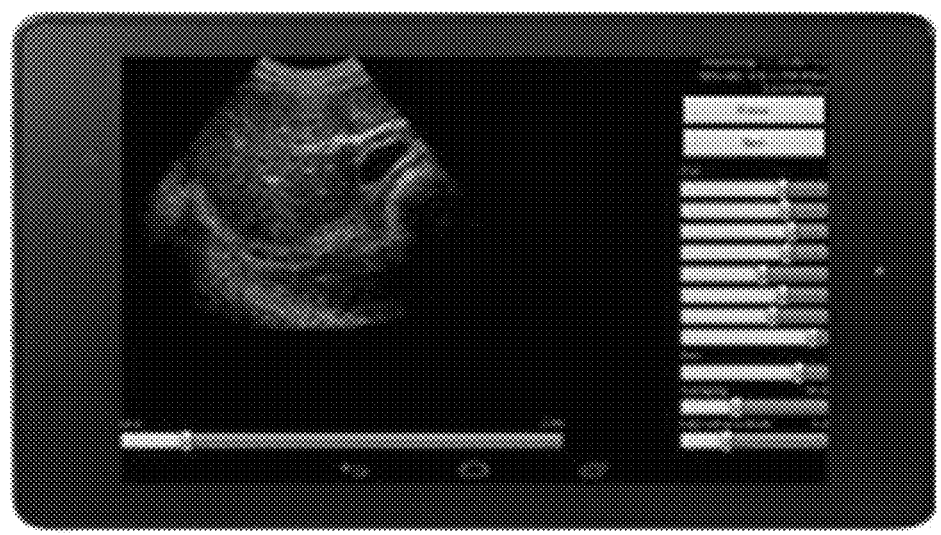
FIG. 10 shows a screen displaying an operation of B-mode imaging operation, obtained by applying the present disclosure.

FIG. 10 shows a screen displaying an operation of B-mode imaging at Nexus7, obtained by applying the present disclosure.

As shown in FIG. 10, the overall time gain compensation is divided into 8 stages so that a user may adjust brightness of an image based on each depth, and the overall gain is also adjustable. A user interface is designed to allow a user to adjust a threshold value for setting the degree of averaging filtering and a weight for setting the degree of edge enhancing.

In addition, the method for high-speed parallel processing for an ultrasonic signal by using a smart device may be stored in a computer-readable recording medium on which a program for executing the method with a computer is recorded. At this time, the computer-readable recording medium includes all kinds of recording mediums storing computer-readable data. The computer-readable recording medium may be, for example, ROM, RAM, CD-ROM, DVD-ROM, DVD-RAM, a magnetic tape, a floppy disk, a hard disk and optical media. In addition, the computer-readable recording medium may be distributed to computer systems connected through a network so that computer-readable codes may be stored and executed in a distribution way.

Even though the embodiments of the present disclosure have been described, the present disclosure is not limited thereto but can be modified in various ways within the technical scope of the present disclosure, which also belongs to the scope of the appended claims.

INDUSTRIAL APPLICABILITY

As described above, in the present disclosure, high-speed parallel processing may be performed to an ultrasonic signal in a smart device by using a GPU, similar to the case in a PC environment. In addition, an ultrasonic image system may have a subminiature design. Also, since many users regardless of age or sex may install software in a simple application form at smart devices widely propagated and also obtain an ultrasonic image by using the software, the present disclosure contributes to cost reduction and popularization of the ultrasonic system. Since data containing information about an ultrasonic image may be received remotely and an ultrasonic image may be obtained by signal processing at the smart device, the propagation of remote medical examination is also expected.

The method for high-speed parallel processing for an ultrasonic signal by using a smart device according to the present disclosure may provide an image of a frame rate useful for medical diagnosis by performing high-speed parallel processing to an ultrasonic signal by means of a mobile GPU in a smart device even in a mobile-based environment, other than a PC-based environment.

In addition, the method for high-speed parallel processing for an ultrasonic signal by using a smart device according to the present may distribute operations required for parallel processing of ultrasonic signals and thus process the ultrasonic signals more rapidly by allowing a part of calculations allocated to a fragment shader stage in a graphics pipeline structure to be performed in a vertex shader stage, when the ultrasonic signals are processed in parallel by using the graphics pipeline structure.

The invention claimed is:

1. A method for high-speed parallel processing for an ultrasonic signal by using a smart device, which is used for a smart device having a mobile GPU (Graphic Processing Unit) to receive an ultrasonic signal and generate an ultrasonic image, the method comprising:

by the smart device, receiving a beam-formed ultrasonic signal through a first render cycle, removing a DC component from the ultrasonic signal, and then dividing and outputting an in-phase component and a quadrature component from the ultrasonic signal free from the DC component;

by the smart device, performing quadrature demodulation processing and envelope detection processing through a second render cycle to the ultrasonic signal having the in-phase component and the quadrature component; and by the smart device, performing scan conversion through a fifth render cycle to the ultrasonic signal obtained as a result of the second render cycle, wherein one or more of the render cycles has a graphics pipeline structure including a vertex shader stage, a rasterizer stage and a fragment shader stage, wherein the mobile GPU controls a part of operations allocated to the fragment shader stage to be performed in advance in the vertex shader stage.

2. The method for high-speed parallel processing for an ultrasonic signal by using a smart device according to claim 1, wherein in the vertex shader stage, the mobile GPU receives a plurality of vertexes, allocates a spatial region by using the received vertexes, and then calculates a spatial coordinate for the allocated spatial region to generate a calculation result in the form of a varying parameter.

3. The method for high-speed parallel processing for an ultrasonic signal by using a smart device according to claim 2, wherein in the rasterizer stage, the mobile GPU searches an on-screen coordinate value corresponding to the varying parameter output in the vertex shader stage, and generates the searched coordinate value in the form of a varying parameter.

4. The method for high-speed parallel processing for an ultrasonic signal by using a smart device according to claim 3, wherein in the vertex shader stage, the mobile GPU further calculates a coordinate value located on the periphery of the on-screen coordinate value generated in the rasterizer stage, and generates a calculation result in the form of a varying parameter.

5. The method for high-speed parallel processing for an ultrasonic signal by using a smart device according to claim 4, wherein in the fragment shader stage, the mobile GPU calculates a color for the on-screen coordinate value generated in the rasterizer stage and generates a calculation result.

6. The method for high-speed parallel processing for an ultrasonic signal by using a smart device according to claim 5, further comprising:
by the mobile GPU, storing the color calculation result for the on-screen coordinate value generated in the fragment shader stage in a frame buffer.

7. The method for high-speed parallel processing for an ultrasonic signal by using a smart device according to claim 2, wherein 8 to 16 varying parameters are output depending on a specification of the mobile GPU.

8. The method for high-speed parallel processing for an ultrasonic signal by using a smart device according to claim 1, wherein when an image generated in a previous render cycle is stored in a frame buffer, the mobile GPU transfers the stored image to a texture corresponding to a memory of the mobile GPU by means of a RTT (Render To Texture) technique, and transfers the transferred image to a fragment shader stage in a graphics pipeline of a next render cycle.

9. The method for high-speed parallel processing for an ultrasonic signal by using a smart device according to claim 1, wherein the mobile GPU performs parallel processing to an ultrasonic signal by using a fixed function pipeline structure.

10. The method for high-speed parallel processing for an ultrasonic signal by using a smart device according to claim 1, wherein the method is implemented under OpenGL ES environment.

11. The method for high-speed parallel processing for an ultrasonic signal by using a smart device according to claim 1, wherein in the second render cycle, the smart device further performs decimation processing to the ultrasonic signal to which the quadrature demodulation processing is performed.

12. The method for high-speed parallel processing for an ultrasonic signal by using a smart device according to claim 1, wherein in the second render cycle, the smart device further performs log compression processing to the ultrasonic signal to which the envelope detection processing is performed.

13. The method for high-speed parallel processing for an ultrasonic signal by using a smart device according to claim 12, wherein in the second render cycle, the smart device further performs gain control processing to control an overall gain of an image with respect to the ultrasonic signal to which the log compression processing is performed.

14. The method for high-speed parallel processing for an ultrasonic signal by using a smart device according to claim 1, wherein after the second render cycle is performed, the smart device further performs removing a blackhole for the ultrasonic signal by receiving a threshold value which is regarded as a blackhole through a third render cycle and comparing sizes of the threshold value and the ultrasonic signal received in the second render cycle with each other.

15. The method for high-speed parallel processing for an ultrasonic signal by using a smart device according to claim 1, wherein after the second render cycle is performed, the smart device further performs edge enhancing through a fourth render cycle to the ultrasonic signal received in the second render cycle.

16. A non-transitory computer-readable recording medium, on which a program for executing the method defined in claim 1 with a computer is recorded.

17. A method for high-speed parallel processing for an ultrasonic signal by using a smart device, which is used for a smart device having a mobile GPU (Graphic Processing Unit) to receive an ultrasonic signal and generate an ultrasonic image, the method comprising:
by the smart device, receiving a beam-formed ultrasonic signal through a first render cycle, removing a DC component from the ultrasonic signal, and then dividing and outputting an in-phase component and a quadrature component from the ultrasonic signal free from the DC component;
by the smart device, performing quadrature demodulation processing and envelope detection processing through a second render cycle to the ultrasonic signal having the in-phase component and the quadrature component; and
by the smart device, performing scan conversion through a fifth render cycle to the ultrasonic signal obtained as a result of the second render cycle,
wherein one or more of the render cycles has a graphics pipeline structure including a vertex shader stage, a rasterizer stage and a fragment shader stage, and
wherein after the second render cycle is performed, the smart device further performs removing a blackhole for the ultrasonic signal by receiving a threshold value which is regarded as a blackhole through a third render cycle and comparing sizes of the threshold value and the ultrasonic signal received in the second render cycle with each other.

18. The method for high-speed parallel processing for an ultrasonic signal by using a smart device according to claim 17, wherein after the second render cycle is performed, the smart device further performs edge enhancing through a fourth render cycle to the ultrasonic signal received in the second render cycle.

19. A method for high-speed parallel processing for an ultrasonic signal by using a smart device, which is used for a smart device having a mobile GPU (Graphic Processing Unit) to receive an ultrasonic signal and generate an ultrasonic image, the method comprising:
by the smart device, receiving a beam-formed ultrasonic signal through a first render cycle, removing a DC component from the ultrasonic signal, and then dividing and outputting an in-phase component and a quadrature component from the ultrasonic signal free from the DC component;
by the smart device, performing quadrature demodulation processing and envelope detection processing through a second render cycle to the ultrasonic signal having the in-phase component and the quadrature component; and by the smart device, performing scan conversion through a fifth render cycle to the ultrasonic signal obtained as a result of the second render cycle, wherein one or more of the render cycles has a graphics pipeline structure including a vertex shader stage, a rasterizer stage and a fragment shader stage, and wherein after the second render cycle is performed, the smart device further performs edge enhancing through a fourth render cycle to the ultrasonic signal received in the second render cycle.

20. The method for high-speed parallel processing for an ultrasonic signal by using a smart device according to claim 19, wherein the mobile GPU controls a part of operations allocated to the fragment shader stage to be performed in advance in the vertex shader stage, and wherein after the second render cycle is performed, the smart device further performs removing a blackhole for the ultrasonic signal by receiving a threshold value which is regarded as a blackhole through a third render cycle and comparing sizes of the threshold value and the ultrasonic signal received in the second render cycle with each other.

* * * * *